(12) United States Patent
Dilmanian

(10) Patent No.: US 7,643,610 B2
(45) Date of Patent: Jan. 5, 2010

(54) METHOD AND DEVICES FOR PERFORMING STEREOTACTIC MICROBEAM RADIATION THERAPY

(75) Inventor: F. Avraham Dilmanian, Yaphank, NY (US)

(73) Assignee: Brookhaven Science Associates, LLC, Upton, NY (US)

( * ) Notice: Subject to any disclaimer, the term of this patent is extended or adjusted under 35 U.S.C. 154(b) by 264 days.

(21) Appl. No.: 11/867,233

(22) Filed: Oct. 4, 2007

(65) Prior Publication Data

US 2009/0093863 A1    Apr. 9, 2009

(51) Int. Cl.
*A61N 5/10*    (2006.01)
(52) U.S. Cl. .......................................... 378/65; 378/193
(58) Field of Classification Search ...................... 378/9, 378/65, 119, 121, 145, 193–198
See application file for complete search history.

(56) References Cited

U.S. PATENT DOCUMENTS 5,339,347 A    8/1994    Slatkin et al. .................. 378/65

7,158,607 B2    1/2007    Dilmanian et al. ............ 378/65
7,194,063 B2    3/2007    Dilmanian et al. ............ 378/65

FOREIGN PATENT DOCUMENTS

WO    WO 2006/086630    8/2006
WO    WO 2006/086631    8/2006

OTHER PUBLICATIONS

Phillips et al., "The Response of $CD24^{-/low}/CD44^+$ Breast Cancer-Initiating Cells to Radiation," Journal of the National Cancer Institute, vol. 98, No. 24, Dec. 20, 2006.

*Primary Examiner*—Courtney Thomas
(74) *Attorney, Agent, or Firm*—Dorene M. Price

(57) ABSTRACT

A radiation delivery system generally includes either a synchrotron source or a support frame and a plurality of microbeam delivery devices supported on the support frame, both to deliver a beam in a hemispherical arrangement. Each of the microbeam delivery devices or synchrotron irradiation ports is adapted to deliver at least one microbeam of radiation along a microbeam delivery axis, wherein the microbeam delivery axes of the plurality of microbeam delivery devices cross within a common target volume.

25 Claims, 9 Drawing Sheets

METHOD AND DEVICES FOR PERFORMING STEREOTACTIC MICROBEAM RADIATION THERAPY

This invention was made with Government support under contract number DE-AC02-98CH10886, awarded by the U.S. Department of Energy. The Government has certain rights in the invention.

BACKGROUND OF THE INVENTION

The present invention relates generally to devices and methods for performing microbeam radiation therapy on a subject for treatment of tumors and of other diseases, and more particularly to a stereotactic device and method of delivering microbeam arrays from multiple angular directions to produce a broad beam effect only within a target volume thus increasing the therapeutic effect of microbeam radiation therapy.

Cancer continues to be one of the foremost health problems. Conventional treatments such as surgery, chemotherapy and radiation therapy have exhibited favorable results in many cases, while failing to be completely satisfactory and effective in all instances. For example, the effectiveness of orthodox radiation therapy on deep pulmonary, bronchial, and esophageal tumors is limited by the risk of radiation pneumonitis. Also, non-tumor applications of radiation therapy, such as the ablation of epileptogenic foci, are still considered a challenge with conventional radiation therapy and radiosurgery.

The goal of radiation therapy is generally to maximize the therapeutic index, which is defined as the ratio of the maximum tolerable dose beyond which unacceptable levels of normal tissue toxicity would occur, to the minimal dose required for effective tumor control. This goal is particularly difficult to achieve in treating central nervous system (CNS) tumors. Malignant gliomas which include astrocytomas, oligodendrogliomas and glioblastoma represent about 60% of all primary brain tumors, with an incidence of over 8,000 cases per year. The survival statistics of patients with high grade gliomas in the brain, or lower grade gliomas and metastatic tumors in the spinal cord have not improved appreciably in recent years using conventional surgical techniques and conventional radiotherapy. The doses that can be delivered to malignant CNS tumors are limited by the tolerance of normal brain and spinal cord to radiation. For higher grade CNS tumors, radiation is generally offered only as a palliative rather than curative therapy. For lower grade CNS tumors, the ratio of radiotherapy doses that produce normal CNS toxicity and those that control the tumor is so close that it often renders radiotherapy ineffective, or results in neurological complications from radiotoxicity to the normal CNS surrounding the tumor. In addition, tolerance of the normal CNS to re-treatment, if necessary, will be lower.

Conventional radiation therapy has serious limitations due to radiation damage to normal tissues. Although stereotactic radiosurgery has improved the outcomes, highly radiosensitive structures located in the vicinity of the target remain a limiting factor. It is well known to those skilled in the art that the threshold dose, or maximum tolerable dose before neurological and other complications of radiotherapy arise, increases as irradiated volumes of tissue are made smaller. Such observations eventually led to the development of grid radiotherapy using grids or sieves for spatial fractionation of X-rays.

Recently, a much less familiar alternative form of radiation therapy, known as microbeam radiation therapy (MRT), has been investigated in laboratory animals to treat tumors such as those for which the conventional methods are ineffective or associated with a high risk factor. The concept of MRT was introduced in U.S. Pat. No. 5,339,347 to Slatkin et al. MRT differs from conventional radiation therapy by employing arrays of parallel planes of radiation, which are at least one order of magnitude smaller in thickness (or diameter if, in the rare case, parallel cylindrical beams are used rather than planar beams) than the smallest radiation beams in current conventional clinical use. These very thin microbeams, which are also called microplanar beams, can be generated using the high intensity X-ray beams that are currently generated at electron synchrotron storage rings.

There are three disadvantages of the broad beams currently used in clinical radiation therapy over microbeams. First, they do not allow treatment of very small targets (because of their size limit), and they give additional dose to the neighboring non-targeted tissue (because of their un-sharp edges). Second, they will not have the tissue-sparing effect of x-ray microbeams (or microplanar beams) that are possessed only by sub-millimeter or millimeter beams. Third, they are usually administered in many dose fractions, which is often difficult on the patent.

The Slatkin et al. patent discloses the segmentation of a broad beam of high energy X-ray into arrays of parallel microbeams (beams of thickness less than about 1 millimeter (mm)), and a method of using the microbeams to perform radiation therapy. The target tissue, e.g., a tumor, receives a summed absorbed dose of radiation exceeding a maximum absorbed dose tolerable by the target tissue by crossing or intersecting the microbeam arrays at the target tissue. The irradiated in-path non-target tissue is exposed only to non-crossing beams. Non-target tissue between the microbeams receives a summed absorbed dose of radiation less than the maximum tolerable dose, i.e., a non-lethal dose to non-target tissue. In this way, the irradiated non-target tissue in the path of the microbeam is allowed to recover from any radiation injury by regeneration from the supportive cells surviving between microbeams. The probability of radiation-induced coagulative necrosis in the irradiated normal, non-targeted tissue is also lowered due to the non-crossing beam geometry in the non-target tissue, allowing for lower levels of radiation to the non-target tissue. Using microbeam radiation therapy in this way helps improve the effectiveness of clinical radiation therapy, especially for deep-seated tumors. Finally, it was shown that microbeams have a "preferential tumoricidal effect", i.e., they damage the tumor preferentially while sparing the surrounding normal tissues. This effect, observed in tumor-bearing rats and mice irradiated with microbeam, arrays from a single direction, has an important implication on the present patent.

The microbeams geometries disclosed in the Slatkin et al. patent are of two basic types. Exposure of the target may be accomplished by a unidirectional array of microbeams which may be parallel or may converge at the target. Alternatively, two arrays of microbeams originating from different directions may be "cross-fired," and intersect at an isocenter in the target tissue. The microbeams within each array may be substantially parallel to each other or may converge at an isocenter within the target.

Commonly owned U.S. Pat. Nos. 7,158,607 and 7,194,063 to Dilmanian, the specifications of which are incorporated herein by reference, disclose improvements on the MRT method disclosed in the Slatkin et al. patent. In U.S. Pat. No. 7,158,607, two arrays of microbeams are interlaced or interleaved at a target tissue to produce a continuous broad beam effect only within the target volume. In U.S. Pat. No. 7,194, 063, a method of administration of microplanar beam arrays was shown that was particularly useful for assisting recovery of a damaged spinal cord and a brain.

An important concept in microbeam radiation therapy is the "valley dose". It is the radiation leakage between the beams caused mostly by x-ray scattering. For the normal tissues surrounding the target to be spared from the radiation, the valley dose in the normal tissue should be adequately low to allow the supportive cells to survive.

There is a need in the prior art for further improvements of radiation therapy, as well as efficient devices for implementing MRT, which greatly enhance the therapeutic dose at a target, while simultaneously maintaining a safe dose to normal tissue. There is also a need, which is lacking in the prior art, for an effective system to perform multiple-angle delivery of microbeams simply on tissues affected by diseases and conditions without inducing radiation injury to surrounding healthy tissue.

SUMMARY OF THE INVENTION

The present invention, which addresses the needs of the prior art, relates to a system and more efficient methods of radiation therapy which greatly enhance the therapeutic dose and damage to target tissue, such as a tumor, while simultaneously reducing damage to normal tissue in the path of the irradiating beam. This result is achieved by a radiation delivery gantry, which generally includes a support frame and a plurality of microbeam delivery devices supported on the support frame in a hemispherical arrangement. Each of the microbeam delivery devices is adapted to deliver at least one microbeam of radiation along a microbeam delivery axis, wherein the microbeam delivery axes of the plurality of microbeam delivery devices cross within a common target volume.

In a preferred embodiment, each of the microbeam delivery devices is an orthovoltage x-ray tube, and the radiation is x-ray radiation. Preferably, at least one pair of the microbeam delivery devices is orthogonally arranged so that the microbeam delivery axes of the pair cross within the target volume at a ninety degree angle. In this regard, there are preferably five pairs of orthogonally arranged devices and the microbeam delivery axes of any two adjacent microbeam delivery devices cross within the target volume at about a forty-five degree angle.

Also in the preferred embodiment, each of the microbeam delivery devices is adapted to deliver a two-dimensional array of substantially parallel cylindrical microbeams, also called pencil beams, to the target volume. The cylindrical beams in each array are preferably arranged in a square pattern of rows and columns, wherein the cylindrical microbeams have a diameter less than 1 mm and are spaced in each of the two directions of rows and columns, with less than 3 mm on center, but at least twice the beams' diameter. The cross sections of the pencil beams, nominally circular, can also be square, elliptical, or rectangular.

The microbeam arrays preferably include a first array having at least a first and a second cylindrical microbeam and a second array having a third microbeam. The first and second microbeams define two parallel, spatially distinct microbeam paths, and the third microbeam defines a third microbeam path, wherein the first and second microbeam arrays are interlaced substantially only within the target volume. The third microbeam path is orthogonal and laterally translated with respect to the first and second microbeam paths, whereby the third microbeam path crosses between but does not intersect with the first and second microbeam paths to form a substantially continuous broad beam of radiation substantially only within the target volume. In this manner, the microbeam delivery devices will deliver the two-dimensional arrays in a pattern covering a continuous solid angle of $2\pi$ steradian around the target volume.

In an alternative embodiment, the x-ray microbeams are produced by a fixed synchrotron source. In this embodiment, an angularly displaceable patient bed establishes a plurality of microbeam delivery angles supported in a hemispherical arrangement. Each of the microbeam delivery angles is adapted to deliver at least one microbeam of radiation along a microbeam delivery axis, wherein the microbeam delivery axes of the plurality of microbeam delivery angles cross within a common target volume. In this embodiment, the microbeam delivery device preferably uses a magnet called a wiggler in an electron storage ring. In this embodiment the beam's direction is fixed in space (preferably beam propagating either horizontally or vertically) and the subject is positioned on (and tightly attached to) a couch that can assume different positions and angles with respect to the beam. The location of the individual microbeam delivery devices, or their angles (in a synchrotron-based system), is referred to in the specification at times as a "port."

The present invention further involves a method for delivering x-ray radiation. The method generally includes the step of aiming an array of substantially parallel, cylindrical x-ray microbeams at a target from a plurality of angularly spaced directions with respect to the target, wherein the arrays define a hemispherical arrangement of delivery ports around the target. The x-ray microbeams may be provided by a fixed synchrotron source, wherein the aiming step includes the step of tilting a patient bed different angles in front of the array for implementing different irradiation ports. Alternatively, the x-ray microbeams may be provided by a plurality of orthovoltage x-ray tubes.

In the method of radiation therapy according to the present invention, the number of ports can be increased up to 14, producing up to seven pairs of nearly orthogonal pairs. In this geometry the angle between the adjacent ports will be as small as about 30°.

The present invention also involves a method for treating breast cancer. The method generally includes the steps of providing a plurality of x-ray microbeam delivery ports in a hemispherical arrangement around a breast having a tumor and delivering at least one x-ray microbeam from each of at least one pair of orthogonally arranged delivery ports into the breast tumor. Each of the delivery ports is adapted to deliver at least one x-ray microbeam along a microbeam delivery axis, wherein the microbeam delivery axes of the plurality of delivery ports cross within the breast tumor, and wherein the microbeam delivery axes of the orthogonal pair cross within the breast tumor at a ninety degree angle.

As a result, the present invention provides more efficient methods of radiation therapy by employing microbeams in particular geometries. The ten irradiations can be given in one session, or at the most in five sessions (i.e., the two interlacing arrays in each of the five orthogonal pairs of ports must be given in one session for targeting precision)

The preferred embodiments of the stereotactic microbeam radiation therapy system and method of the present invention, as well as other objects, features and advantages of this invention, will be apparent from the following detailed description, which is to be read in conjunction with the accompanying drawings. The scope of the invention will be pointed out in the claims.

DETAILED DESCRIPTION OF THE INVENTION

The present invention involves a clinical radiosurgery system producing thick microbeams, i.e., nearly 1 mm in diameter, in a stereotactic geometry. The method is called stereotactic microbeam radiation therapy (SMRT). Depending on the type of the x-ray source used, two different SMRT systems are disclosed, namely the x-ray-tube-based SMRT and the synchrotron-based SMRT.

Figure 1:
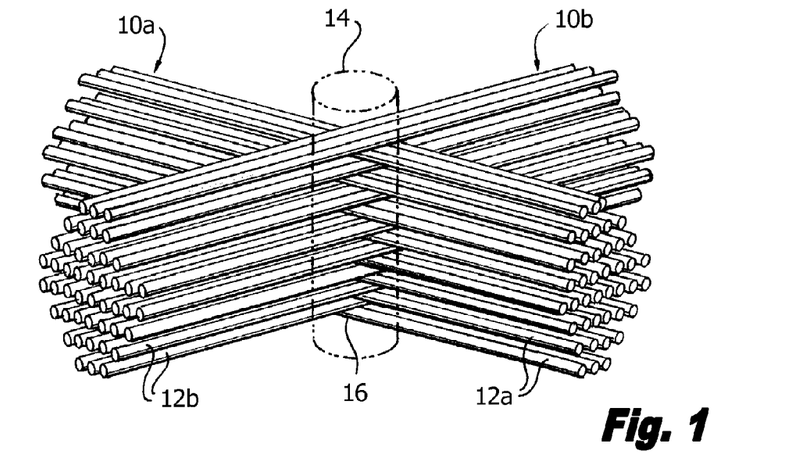
FIG. 1 is a perspective view of two interlacing arrays of pencil microbeams from one of the five orthogonal pairs of ports of the gantry formed in accordance with the present invention.

In a preferred embodiment, each quasiparallel beam array is produced by an individual x-ray tube aimed at the target from a certain direction. Thus, as shown in FIG. 1, two arrays 10 of quasiparallel pencil microbeams 12 are aimed at a target 14 from two orthogonal directions. The beams 12 in each array are preferably about 0.6 mm in diameter and are preferably spaced in a square two-dimensional x-y pattern at about 1.5 mm on-center in both x and y directions. The first microbeam array 10a is interleaved or interlaced with the second microbeam array 10b to form a substantially continuous three dimensional irradiation pattern at the target with half the beam spacing between the planes of microbeams, making these microbeams touch at the edges. This produces a rather dense and nearly uniform pattern 16 of radiation only within the target tissue 14.

The implementation of the preferably interleaved arrays 10a and 10b is achieved first by having the propagation planes of the rows of microbeams in the two arrays parallel to each other, and, second, by having one array shifted with respect to the other in the direction perpendicular to the rows by half the amount of beam spacing on-center. The latter effect is implemented differently in the x-ray-tube-based system and the synchrotron-based system. In the x-ray-tube-based SMRT the multi-hole collimators in each pair of orthogonal tubes are pre-arranged in the interlacing geometry by incorporating the necessary shift between the rows of the microbeams (collimators not shown in FIG. 1).

In the synchrotron-based SMRT, however, the instantaneous beam array produced is not two-dimensional but one-dimensional. This is because the synchrotron beam has inherently a fan-shaped geometry with a fan's height of only a millimeter or two. Also, the synchrotron beam is fixed in the space and cannot be moved. Therefore, when using the synchrotron source the two-dimensions arrays of microbeams is produced by translating the subject stepwise in front of the beam after the exposure to each row of microbeams (i.e., closing a fast shutter after the exposure to one microbeam row, shifting the subject by the amount of beam-spacing on-center, and opening the fast shutter again for exposing the next microbeam row). Here, the interlacing of the orthogonal arrays is implemented by first exposing the patient to the first array, then changing the position of the patient's couch to the second irradiation angle, then shifting the patient's couch laterally to the beam by half the on-center beam spacing between the rows, and then exposing the patient to the second array.

In each case, the method according to the present invention involves the effective translation of the respective microbeams relative to each other by at least a beam thickness, and angularly displacing, i.e., positioning one x-ray delivery device from another along a plane parallel to the irradiation paths of the microbeams. The axis of rotation about which the arrays 10a and 10b are positioned is preferably positioned through the center of the target volume 14, and perpendicular to the microbeam axes. In this way, the beams 12a of the array 10a in the first irradiation direction preferably remain substantially parallel to the beams 12b of the second array 10b after rotation.

In addition, the arrays 10a and 10b are non-intersecting arrays. In other words, the axes of the individual beams 12a of the first array 10a do not intersect the axes of any of the beams 12b of the second array 10b within the irradiated subject.

Figure 2A:
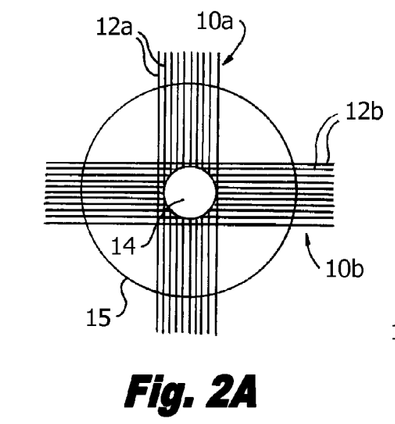
FIG. 2a is a top view of two arrays of pencil microbeams aimed at the target at a ninety degree angle.
Figure 2B:
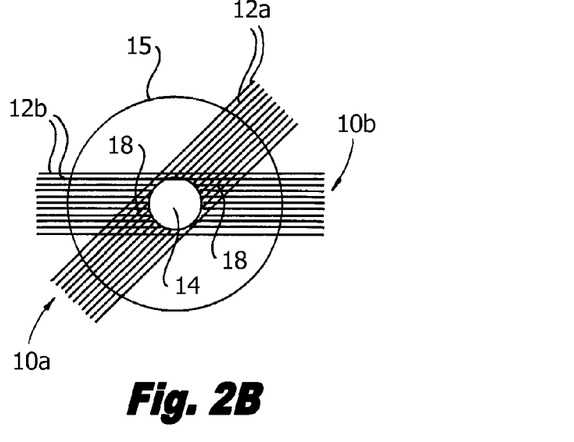
FIG. 2b is a top view of two arrays of pencil microbeams aimed at the target at a forty-five degree angle.

Referring additionally to FIG. 2a, it has been found that the optimal irradiation pattern is to use two arrays 10a and 10b positioned exactly 90° to each other to minimize "array crossing." Referring to FIG. 2b, it has been further found that the minimum angle for delivering adjacent beam arrays 10a and 10b will require that any array crossing will be occurring at an angle at or near 45°. This will produce minimal beam crossover areas 18 outside the target tissue 14.

The term "array crossing" refers to the triangular regions 18 adjacent to the target volume 14 in the normal tissue 15 where two microbeam arrays 10a and 10b cross each other. The inner circle is the target 14 and the outer circle is the subject 15. FIG. 2a shows an array crossing at 90 degrees, where the array crossing is negligible and FIG. 2b shows an array crossing at 45 degrees, where the array crossing is at a minimum. Referring to FIG. 2b, it has been further found that the second best angle for producing minimum array crossing in delivering adjacent beam arrays 10a and 10b is at an angle at or near 45°. This will produce minimal areas region of array crossing 18, i.e., crossing of the arrays outside the target tissue 14. The reason for designing the system for a minimum array crossing is that it produces twice a larger value of "valley dose" in the normal tissue than single arrays. This valley dose, still tolerable to the normal tissues, ideally it should be minimized. The microbeam arrays in the pairs of orthogonal ports substantially interleave (interlace) with each other inside the target, thus most effectively filling the dose vacancy areas in the target.

Irradiation of the target from such angles will produce a dense or "crowded" pattern of radiation, which is composed of: a) direct pencil microbeam hits in the target, some interlacing and some crossing or passing each other at close proximity; and b) their associated x-ray scattering (Compton Scattering and Coherent Scattering), which is also centered at the target. The latter produces a bell-shaped, smooth dose distribution over which the dose from hits by individual microbeam ride. Furthermore, the finite range of the photoelectrons and Compton electrons also contribute to extra smoothing of the dose distribution in the target. The net result is that a nearly uniform dose distribution is produced at the target with nearly no non-contiguous regions. Therefore, the non-contiguous dose regions, traditionally called the "valley dose" in the old methods of microbeam dose administration, will be essentially non-existing in SMRT. The therapeutic dose to the target is, therefore, the overall dose distribution produced by: a) direct hits from individual microbeams; and b) x-ray scattering. The extra dose-distribution smoothing produced by the photoelectrons and Compton electrons will help minimize the very small regions of dose dip in the target.

On the other hand, the non-targeted tissue will receive: a) direct exposure of only a single microbeam array, with the exception of small regions 18 near the target that receive array-crossings, and b) only the tail of the bell-shaped scattering dose distribution. Therefore, the non-targeted tissue is left with none of very little radiation injury, while the target can receive a lethal dose.

Figure 3:
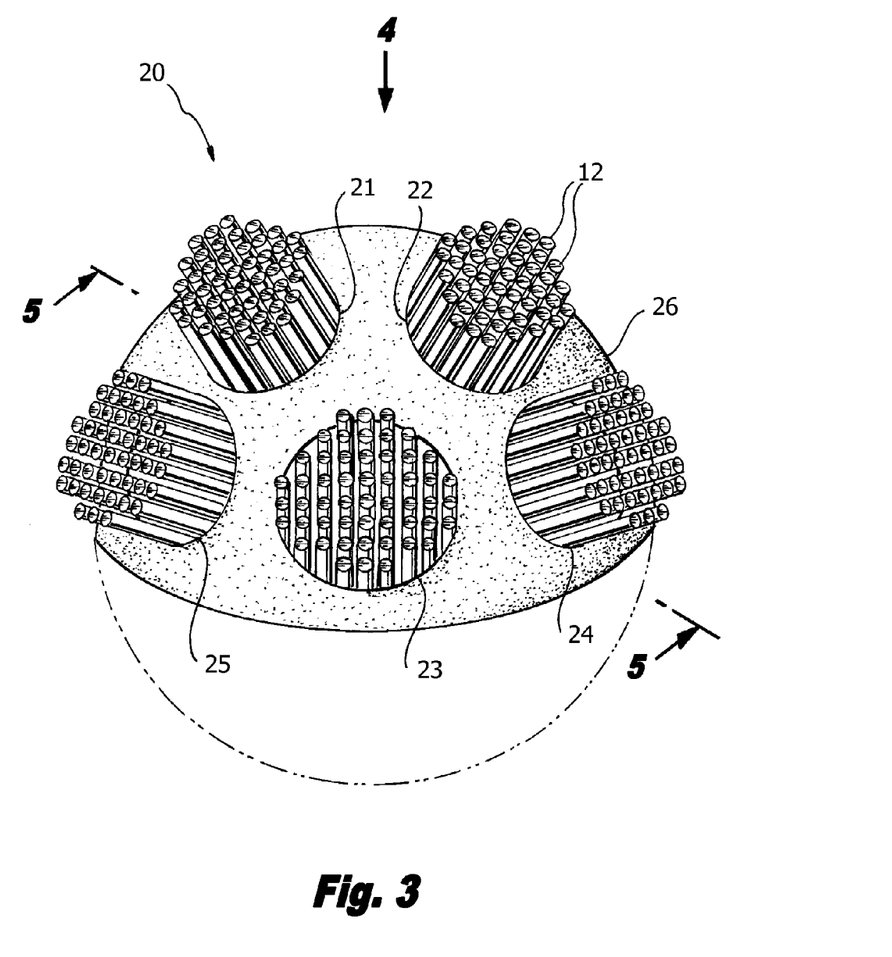
FIG. 3 is a perspective view of a schematic representation of the irradiation geometry of the x-ray microbeam delivery device of the present invention, showing five of the ten irradiation angles.
Figure 4:
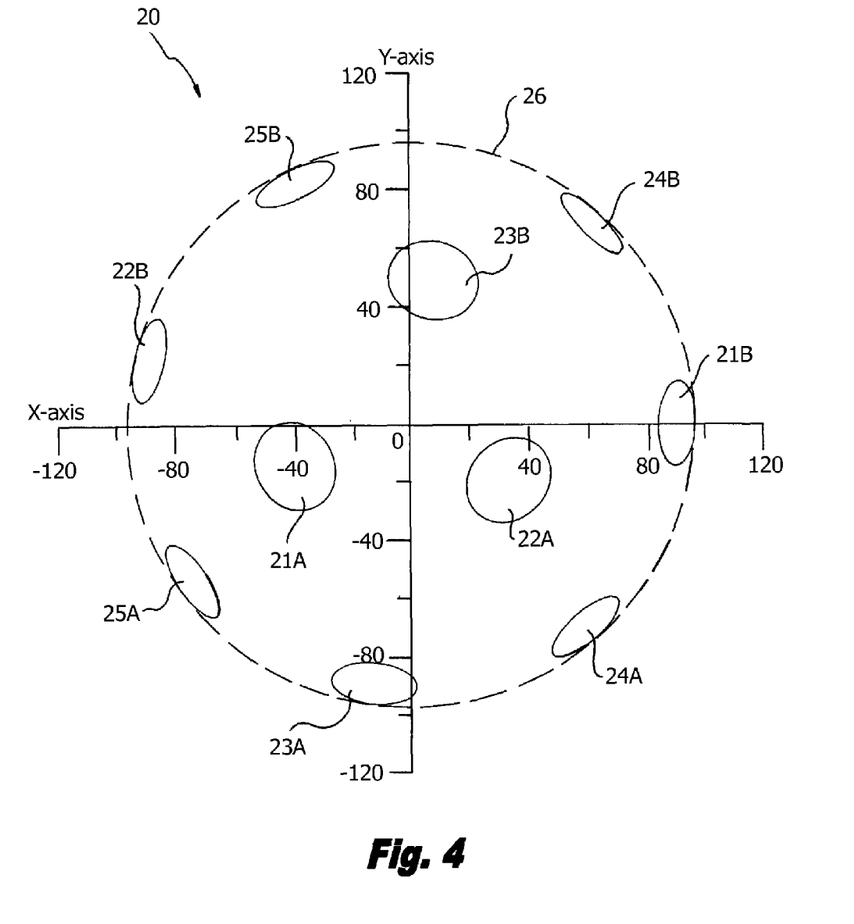
FIG. 4 is a graphical representation of the top view of the x-ray microbeam delivery device shown in FIG. 3 taken along the line 4-4.
Figure 5:
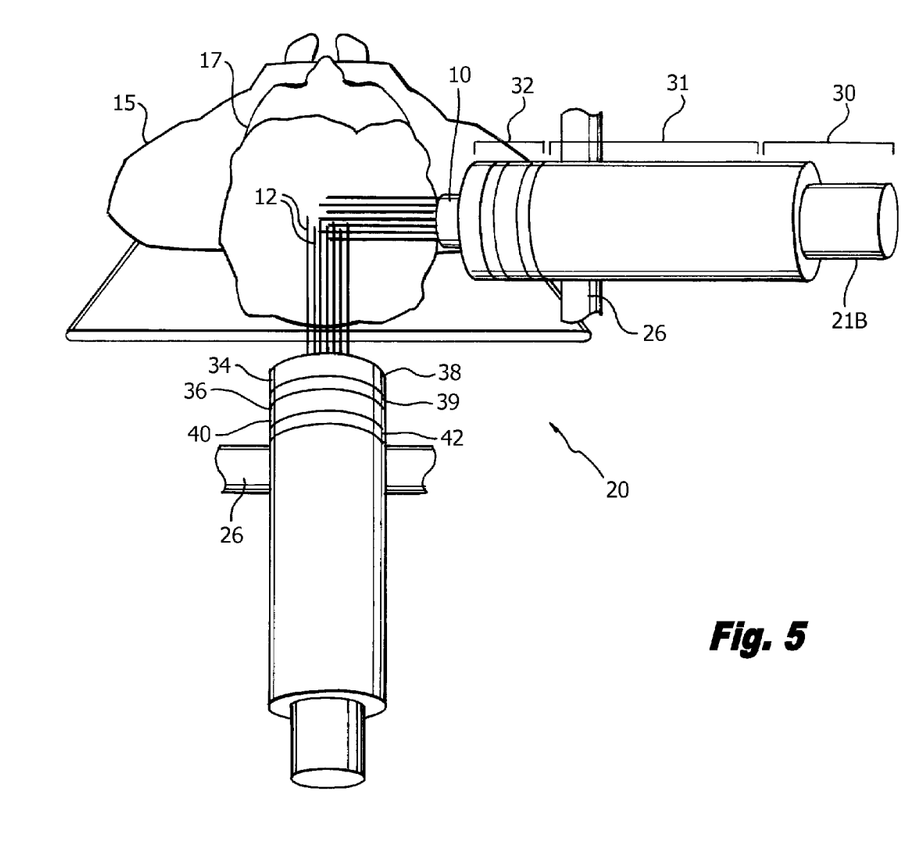
FIG. 5 is a cross-sectional view of the x-ray microbeam delivery device shown in FIG. 3 depicting a pair of orthogonal irradiation angles, taken along the line 5-5 and shown in use with a patient.

Therefore, to the first approximation the preferred design criteria is that a) the angle between each two adjacent arrays is about 45°, and, b) the sources will fill a continuous solid angle of $2\pi$ steradian over the target. Based on these design criteria, it has been found that a structural arrangement of 10 x-ray tubes positioned over a hemi-spherical space is preferred. In other words, it has been found the optimal irradiation protocol with SMRT is achieved by positioning five independent 90° x-ray tube-pairs on a half sphere, as shown in FIGS. 3-5. The use of a full hemi-sphere not only will fully utilize the entrance-dose solid angle available, thus diluting the entrance dose to any tissue, but also excludes the geometries in which two beam arrays are aimed at the target from 180°. The latter prohibition is because such geometry may produce nearly continuous dose distribution (i.e., nearly broad beam) in the normal tissue on the far side of the target volume. This prohibition will be used to the treatment's favor by choosing the radiation delivery side to the area of the body closer to the target.

FIG. 3 is a schematic view of an x-ray delivery gantry 20 according to the present invention, wherein five of the ten x-ray delivery devices 21, 22, 23, 24, 25 are depicted being supported on a frame or shell 26 in a hemispherical arrangement whereby each device is positioned relative to an adjacent device at an angle of about 45°. The other five, not depicted, are supported on the far side of the hemi-sphere. The frame or shell 26 can be of any conventional construction so long as the x-ray delivery devices can be mounted or otherwise supported in the hemispherical arrangement described in further detail below. For example, a plurality of structural cross-members can be welded or otherwise fastened together to form a frame 26 for supporting the x-ray devices. Alternatively, a hemispherical shell can be molded or cast from a suitable material to form a shell structure for supporting the x-ray devices.

FIG. 3 also schematically shows the geometry of the irradiation arrays reaching the subject in the synchrotron-based SMRT system. In that case, however, the beam array will be fixed in space and the subject will be re-positioned in the space in front of the beam after each irradiation angle to produce the right irradiation-array geometries, as will be discussed in further detail below.

Referring to FIG. 4, which is a graphical representation of the locations of the five orthogonal pairs of x-ray delivery devices 21, 22, 23, 24, 25 with respect to the frame 26, each x-ray delivery device 21A, 22A, 23A, 24A, 25A has a matching x-ray delivery device 21B, 22B, 23B, 24B, 25B positioned at a 90° angle with respect thereto on the hemispherical frame 26. Thus, the gantry 20 includes five "pairs" of x-ray delivery devices, wherein each pair is positioned so as to deliver x-rays at a target from 90° directions. (Again, FIG. 4 also illustrates the pattern, on the subject, of the irradiations produced by the synchrotron-based SMRT.)

Using polar coordinates to designate the angular positions of the ten x-ray delivery devices or angles on the "irradiation hemisphere", the Z-axis of the system (which is also the symmetry axis of the hemisphere, and approximately that of the irradiations' pattern) will be the top (i.e., the pole) of the hemisphere. The range of the polar angles ($\theta$) of the ten devices or angles is 20° to 67°, while the azimuthal angles ($\phi$) take angles in the full range of 0° to 360°. Table 1 below sets forth the optimal positioning for each x-ray delivery device.

TABLE 1

| Radiation Port | Polar angle $\theta$ (degrees) | Azimuthal angle $\phi$ |
|---|---|---|
| 21A | 65.7 | 0.0 |
| 21B | 25.4 | 199.2 |
| 22A | 22.8 | 330.1 |
| 22B | 69.9 | 166.8 |
| 23A | 30.2 | 82.1 |
| 23B | 60.3 | 262.4 |
| 24A | 67.8 | 310.2 |
| 24B | 70.4 | 48.4 |
| 25A | 67.9 | 117.0 |
| 25B | 67.9 | 216.0 |

SMRT is a new administration technique of microbeams in which the target is irradiated from ten different directions (called ports in FIG. 4) using two-dimensional arrays of parallel cylindrical beams. Typical beam geometry in each port is 0.6 mm beam diameter 1.5 mm beam spacing in each direction on-center. The ports are spread over one hemisphere and make angles of 45°, 90°, and 135° with each other. They constitute five pairs of orthogonal ports in which the two arrays of pencil beams "interlace" at the target, in order to "fill" the target with a more uniform dose distribution. The interlacing, together with the Compton scattering produced by the hundreds (or thousands) of direct microbeam paths crossing the target, produces a bell-shaped "background dose" that, once combined with the high dose direct-beam paths, produce a therapeutic radiation dose in the target (the direct paths will be numbered in thousands in larger tumors). The surrounding normal tissues, on the other hand, are spared because they are exposed to a single array only, or, in some areas near the target, to two arrays. The latter effect, called "array crossing", relates to small regions at the edge of the target but in the non-targeted tissue where two arrays cross each other. In these regions the "valley dose" is twice higher than that in single arrays; the valley dose is the radiation leakage dose between the direct beams that is produced by Compton scattering or Coherent Scattering as well as the migration paths of the Compton electrons and photoelectrons. The volume of "array crossing" between two arrays is the smallest at 90°, followed by that at 45°, as shown in FIG. 2. In fact this is the reason behind the choice of the inter-port angles of 45° and 90°.

The microbeam arrays preferably include a first array having at least a first and a second cylindrical microbeam and a second array having a third microbeam. The first and second microbeams in the first array define two parallel, spatially distinct microbeam paths, and the third microbeam defines a third microbeam path. For the pairs of orthogonal arrays, the first and second microbeam array are interlaced substantially only within the target volume. For this to happen, all the rows of the cylindrical beams in the two arrays must be propagating in planes parallel to each other, and the rows in one of the two arrays must be shifted in the direction perpendicular to the rows with respect to the rows in the other port by half the spacing on-center between the rows so that the planes of rows in the two arrays interlace. For example, if one of these two arrays happen to be made of two microbeams only (called the first and the second microbeam) and the other arrays is made of one beam only (called the third microbeam), then third microbeam path is orthogonal and laterally translated with respect to the first and second microbeam paths, whereby the third microbeam path crosses between but does not intersect with the first and second microbeam paths to form a substantially a three-dimensional irradiation field made of row and columns of cylindrical beams in which the spacing between the rows is half that in each incident array.

In the above manner, the ten microbeam delivery devices or angles will deliver five pairs of interlacing three-dimensional arrays in a pattern that produces a dense and somehow uniform dose distribution covering an incident solid angle of $2\pi$ steradian around the target volume. This dense radiation, augmented by the "cloud" of scattered radiation in the target volume (from Compton scattering and Coherent Scattering) produce a dose distribution which has a bell-shaped uniform background from scattering over which the high dose from individual microbeams ride. The result is a therapeutic dose to the target, which the not-targeted volumes received only the tail of the scattered radiation (which is tolerable) and exposure to only a single array, or at the most two arrays that occur in certain rather small regions new the target.

FIG. 5 shows the structural arrangement of one orthogonal pair of x-ray delivery devices 21A, 21B mounted on the frame 26. In a preferred embodiment, each x-ray delivery device includes a high current, rotating-anode orthovoltage tube 30 of 150 to 500 kVp as the x-ray source. The tube 30 for each x-ray delivery device 21, 22, 23, 24, 25 is positioned and mounted to the frame in a hemispherical arrangement as described above to interleave the corresponding two non-intersecting arrays substantially only within the target tissue. There is no equivalent to FIG. 5 in the synchrotron-based SMRT system, except that, there, rotating the subject from one angular position to an orthogonal one produces a similar array-interlacing pattern of radiation.

In the x-ray-tube-based system, each x-ray delivery device further includes a front end nozzle 32 located on the side of the tube 30 nearest the patient 15. The nozzle 32 is configured to output the array of x-ray microbeams when irradiated with the x-ray radiation beam produced by the x-ray tube 30. The nozzle 32 preferably includes a multibore collimator 34 and at least one shutter 36. The front end nozzle 32 also preferably includes a dosimetry monitor, such as an ion chamber 38, an edge collimator 39, a bolus 40, as well as an additional shutter (s) 42.

The multibore (or multihole) collimator 34, which can be a tungsten plate in which 0.6-mm holes are made in the square two-dimensional pattern of the microbeams, should be positioned as close as possible to the subject to minimize a beam-widening effect called beam penumbra. On the other hand, the x-ray tube 30 must be located as far as possible from the subject 15 to minimize both the beam penumbra and beam divergence. The piece of tube that connects the x-ray tube with the nozzle is called the separator tube 31.

A nozzle such as that depicted in FIG. 5 will also be used in the synchrotron-based SMRT system. Here, the nozzle will be at the end of the synchrotron beam pipe brining the beam to the patient. Also here, the multi-hole collimator will probably include only one row of holes. It still should be positioned as close as possible to the subject In the tube based system, each x-ray delivery device 21, 22, 23, 24, 25 may be positioned on the frame 26 via a set of stages (not shown), preferably motorized stages, that allows the x-ray delivery devices to be adjusted slightly in terms of angle, the two lateral positions, and distance from the patient 15. Preferably, such changes in position are implemented and monitored with the aid of a computer using techniques well-known to those skilled in the art. Once each device 21, 22, 23, 24, 25 is appropriately aligned, the stages are preferably locked down and fixed on the frame 26 so that the relative positions of the devices with respect to each other do not change during irradiation of the subject 15.

In one embodiment, a single collimating slit can be used with the orthovoltage x-ray tube as the radiation source to create a microplanar beam array in multiple exposures by translating the slit and irradiating the subject 15 multiple times. In this case, the slit is preferably a double-leaf collimator. As known to those skilled in the art, a double-leaf collimator includes two orthogonally positioned collimators which can be independently adjusted in width. This embodiment can be used to produce very small irradiation patterns, i.e., from a few millimeters and on, on the subject, In the preferred embodiment, however, a multi-aperture collimator 34 is positioned in the path of the beam generated by the X-ray source 30 and in front of and close to the subject 15. In this way, a plurality of microbeams 12 are simultaneously produced with one irradiation to form the array 10. The multibore collimator 34 is preferably positioned in the center of the irradiation field that reaches the nozzle 32 and aligned so that its openings are radially positioned to allow maximum transmission of the beam. This collimator will replace the edge collimator 39 described above.

The multibore or multihole collimator 34 and the edge collimator 39 can be made of any material, or combination of materials, in a thickness that will absorb enough x-rays to be completely opaque to the x-rays so that it will that can produce a microbeam(s) from an incident broad beam produced by the x-ray tube or synchrotron with no x-ray penetrations between the beams. Preferred materials include tungsten and lead, with a thickness of at least 10 mm. One skilled in the art will appreciate that the preferred material(s) and thickness will depend primarily on the energy spectrum of the source beam.

The orientation of the collimators 34, 39 (i.e., the azimuthal orientation around the central beam axis) can also be slightly varied using positioning stages for fine-tuning the interlacing geometry. The nozzle 32 may preferably includes tailored edge collimators 34 for each angle to adjust the shape of the beam to the target volume's cross section. Thus, the beam from each port is collimated in a tailored way to conform to the cross section of a tumor 17 when viewing the tumor from that particular angle. The shape, therefore, can be irregular. Furthermore, the depth of the dose penetration for each irradiation angle can be modulated across the field by using tailored boluses for irradiations from each port.

The dosimetry monitor 38 preferably includes any electronic flat dosimetry detector known in the art, for example, an ion chamber. The monitor 38 is preferably positioned as close to the surface of the patient's body as possible in order to accurately monitor the instantaneous dose of radiation administered to the patient 15 by each x-ray tube 30, or port in the synchrotron-based system.

The shutter 36 controls when the patient's exposure to the radiation begins and ends, and thus the length of time of the exposure, by opening and closing the shutter. The shutter 36 is preferably operatively connected to the monitor 38. When the dose reaches a certain pre-set level, as measured by the monitor 38, a shut-off instruction to the system's control is triggered, which, in turn, shuts down the shutter 36 to stop the irradiation.

Preferably, administration of the dose is performed using two shutters 36, 42. One shutter 42 is a slower shutter that stays open during the session and operates as a second layer of safety. The use of such shutters in controlling exposure to x-ray radiation is known to those skilled in the art. The other shutter 36 is a fast shutter, preferably positioned downstream of the slow shutter 42 in the nozzle 32 to more tightly control the exposure time and therefore the dose. The blades of the both shutters 36 and 42 may be made of a heavy metal, such as tungsten, of a thickness capable of stopping the x-rays, generally about 10 mm thick. The mechanical design of the fast shutter 36 preferably utilizes either linear translation of the blades, or rotation of two parallel blades that open and close the shutter by being rotated along an axis parallel to the length of the blades and perpendicular to the beam's axis.

The bolus 40, which is an optional component of the nozzle 32, is formed from a piece of plastic or heavier substance. As known to those skilled in the art, the bolus 40 is shaped to adjust the dose penetration distribution across the irradiation field by preferentially attenuating the incident beam in certain areas of the beam's cross section.

It should be noted that the order of the location of these components as shown in FIG. 5 can be changed without much implication, with one exception: the monitor 38 must, of course, be placed downstream of the shutter(s). In addition, the multibore (or multihole) collimator 34 is preferably positioned as close to the patient's body 15 as possible.

The dose in the target is composed of two components. The first component is the dose from direct microbeams reaching the target volume from different incident angles. Although some of these beams touch each other inside the target, or have overlaps with each other, producing local contiguous-dose areas, in general these beams do not need to all touch each other to produce the treatment dose. Contiguity is produced by the second component of the dose, which is from the x-ray scattering and from the finite range of the photoelectrons and Compton electrons in the tissue. The present invention is based on the concept that, instead of producing a uniform beam with incident beams, one can produce a nearly uniform dose in the target in which the contiguity comes from the scattering and electrons' range that fill the gaps left between the direct passages of the microbeams. Therefore, the implementation of the method requires that the irradiation patterns at the target will be designed in such a way to assure the best continuity among the direct beams, to facilitate the minimizing of "dose dips" in the target. The minimum dose produced in the target should still be large enough to treat the target. For tumor therapy, the microbeams' preferential tumoricidal effect indicated above may prevent the dose dip (s) in the target from interfering with the therapeutic effect of the dose.

Figure 6:
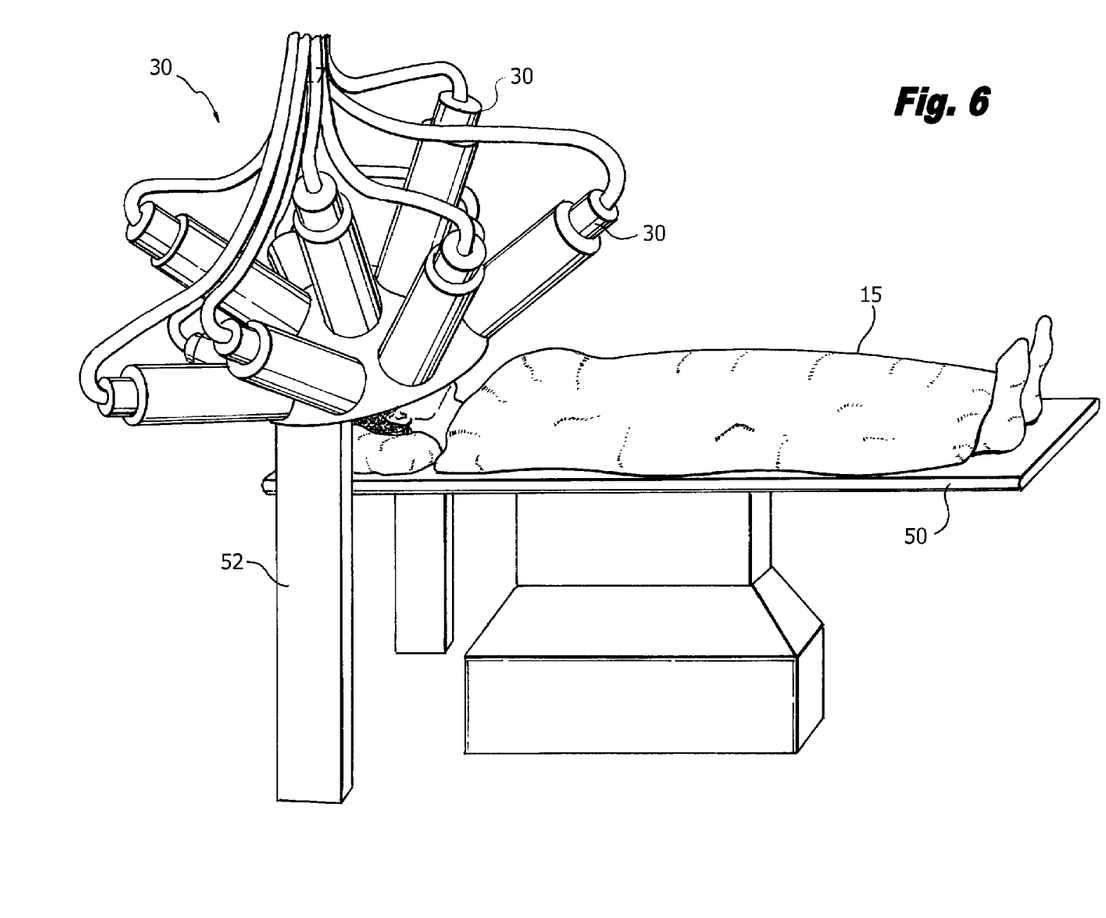
FIG. 6 is a view of an x-ray microbeam delivery facility utilizing a gantry with x-ray tubes as the x-ray source, according to the present invention.

FIG. 6 shows a typical x-ray-tube-based patient treatment facility utilizing a gantry 20 according to the present invention. The system includes a patient bed or couch 50, which can be horizontal or tilted, and a gantry 20 that is positioned above the bed. The bed 50 can also have all possible degrees of motion and rotation to facilitate the aiming of the beams at the target from all possible directions.

The gantry 20 holds the x-ray tubes 30 at their front ends, and each tube is equipped with a front end nozzle 32, as described above, which includes collimators, shutters, etc. Each tube 30 produces either one beam at a time, or an array of quasiparallel beams (pencil beams or circular or square cross sections, or elliptical or elongated beams). The irradiations can be carried out simultaneously with all tubes, or successively with alternate pairs of tubes positioned on the gantry at 90° to each other. The collimator 34 in front of each x-ray tube (positioned very close to the patient to minimize beam penumbra) can be moved to adjust the angle of the beam array. The entire gantry 20 is preferably supported by one or more articulated arms 52, which can rotate and/or re-orient the gantry with respect to the patient 15.

Figure 7:
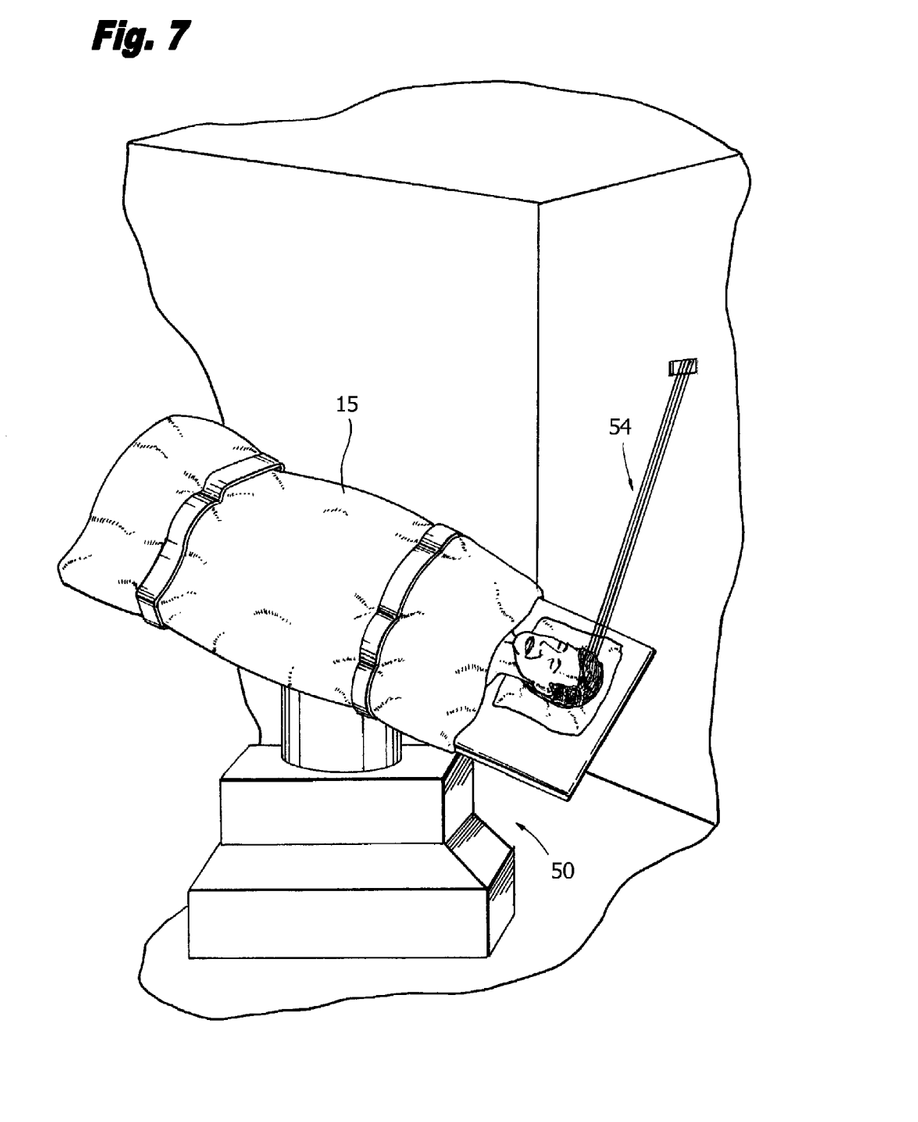
FIG. 7 is a view of an x-ray microbeam delivery facility utilizing a synchrotron as the x-ray source and a patient couch that can assume a wide range of wide angles in front of the fixed beam array.
Figure 8:
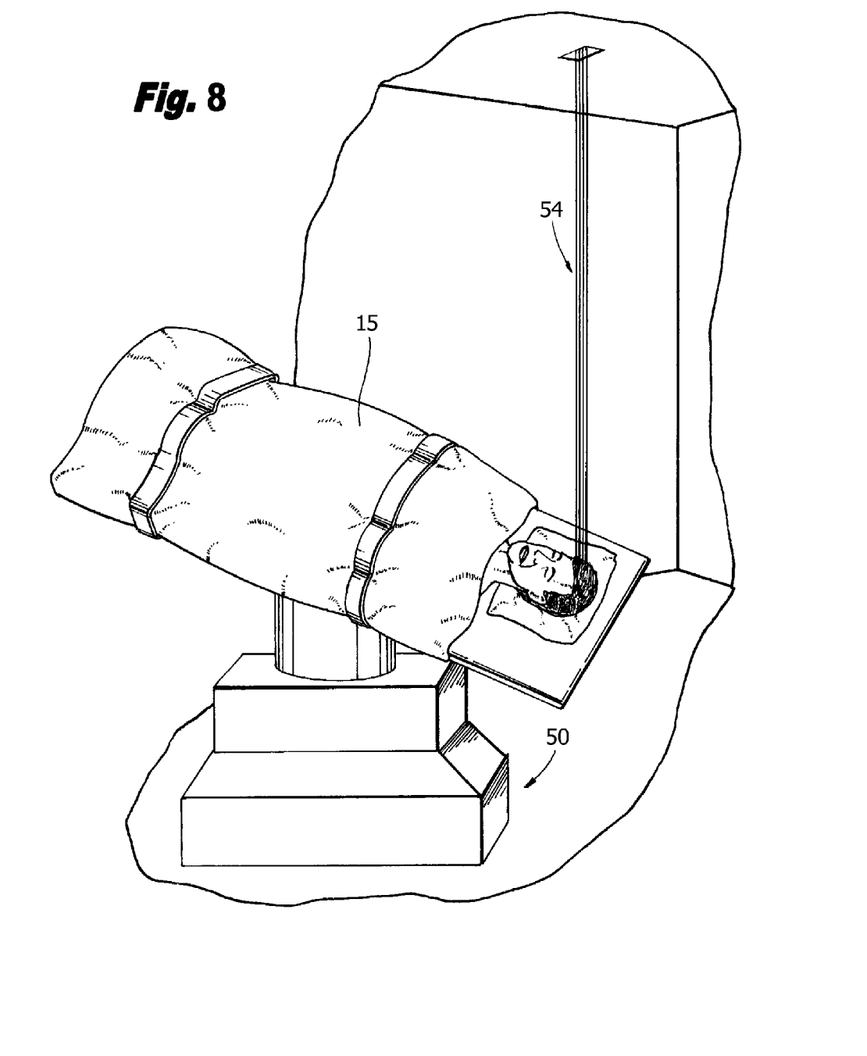
FIG. 8 is a view of an alternative embodiment of an x-ray microbeam delivery facility utilizing a synchrotron as the x-ray source and a patient couch that can assume a wide range of wide angles in front of the fixed beam array.

FIGS. 7 and 8 show an alternative embodiment of a patient treatment facility which utilizes a synchrotron x-ray source, as opposed to x-ray tubes. Synchrotron-based SMRT, as shown in FIGS. 7 and 8, is characterized by a patient couch that is capable of assuming all of the ten SMRT irradiation angles in front of a fixed synchrotron beam 54. Both the x-ray-tube-based SMRT and the synchrotron-based one can be optimally implemented in the treatment of tumors of a) the brain tumors, b) the head and neck tumors, and c) the tumors of the spinal cord.

In the synchrotron-based SMRT the preferential direction of the incident beam 54 is vertical, coming down from the ceiling, as shown in FIG. 8, (or coming up from the floor), for which the following description of the irradiation geometry is made. For the tumors of the brain and the head and neck, the patient 15 will lie on his/her back or front on the couch 50 and his/her head and neck (and to some extent also the rest of his/her body) will be secured to the couch by tight straps. The "pitch" tilt angle of the couch 50, e.g., up-tilt of the bed's head from the horizontal position will then represent the polar angle $\theta$, and therefore will assume values from 20° to 67°. For a given tilt angle, the "yaw" angle $\phi$ will have a certain value. Therefore, a certain combination of couch's $\theta$ and $\phi$ will translate to a certain position of the patient on the couch and the couch itself. For example, defining $\theta=0$ to be the angle in which the patient's face is pointing to the incoming beam from the ceiling (or from the floor), and $\phi=0$ to be the yaw angle of the bed in which the bed points to the north, the angular position $\theta=20°$ and $\phi=0°$ means that the bed's head is tilted 20° upwards. Similarly, the angular position $\theta=67°$ and $\phi=180°$ means that the bed's head is tilted 67° upward and pointing to the south.

The horizontally propagating synchrotron-beam is also an option, as shown in FIG. 7. In this geometry, when treating the tumors of the spinal cord, the patient will be sitting upright on a chair with his/her back generally towards the beam (within the limits of the tilt angle). The Z-axis is now perpendicular to his/her back. Here, the angle $\theta$ is presented by the tilt of the chair forward or backward from the vertical position, while the φ angle presents the chair's rotation around the Z-axis. In other words, the "irradiation hemisphere" in now positioned over the back of the patient.

Because the synchrotron radiation is in the shape of a narrow, fan-shaped beam 54, (commonly horizontal in horizontally propagating synchrotron beams), the two-dimensional arrays of pencil-shaped microbeams that constitute each exposure are administered line by line, using horizontal line (or vertical line, depending on the synchrotron design), and a "step-and-shoot" irradiation configuration. The patient is moved vertically up (or down, or laterally, depending on the synchrotron design) after exposure to each line of pencil beams. The shape of the array, however, generally is not square, but an irregular shape that conforms to the cross section of the target as viewed from the irradiation angle. Therefore, before administering each line of the pencil beams the width of the line is adjusted to the desire width of the array at that height. This adjustment is implemented by moving two collimating "leaves" in and out of the array, the same way multi-leaf collimators are used to adjust the shape of two-dimensional radiation fields. These collimators are called "pair-leaf collimators.

Table 2 sets forth typical design parameters of a synchrotron based system according to the present invention.

TABLE 2

| Parameter | Value |
| --- | --- |
| Synchrotron numbers: Electron storage ring energy | 3 GeV |
| Ring current | 500 mA |
| Beam renewal | Using "top-off" method of beam refilling once every 10 minutes |
| Number of bending magnets | 16 |
| Number of superconducting wigglers (i.e., treatment rooms) | 6 |
| Magnetic field on each wiggler | 6 tesla |
| Number of poles in each wiggler | Up to 30 |
| RF frequency | 500 MHz |
| Ring's circumference | 170 m |

Figure 9:
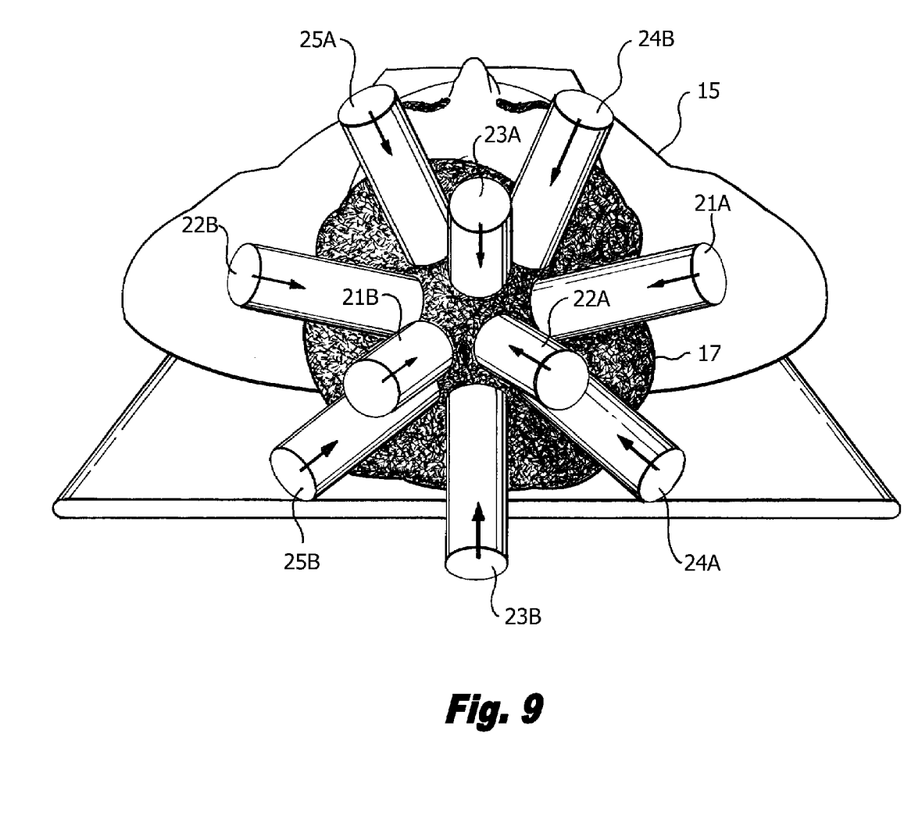
FIG. 9 is an end view of a patent being irradiated with multiple arrays of microbeams delivered by a gantry according to the present invention.

One possible source of x-rays for synchrotron-based SMRT is a wiggler insertion device in a beamline of an electron storage ring of an X-ray synchrotron. A wiggler is a periodic magnet positioned in which consecutive segments have a different direction of magnetic field. It is an "insertion device" because it is inserted in a straight section of an electron storage ring, i.e., between two "bending magnets". An exemplary beam source is the superconducting wiggler of the X17B beamline of the National Synchrotron Light Source at Brookhaven National Laboratory, Upton, N.Y. A conventional "planar" wiggler uses periodic transverse magnetic fields to produce a beam of rectangular cross-section, typically having a horizontal to vertical beam opening angle ratio on the order of 50:1. In an alternative embodiment, the radiation beam is obtained from a "helical" wiggler, a configuration capable of producing a beam with a more isotropic two-dimensional cross section, (i.e., nearly a square beam instead of a narrow fan-shaped beam). It is possible to use a helical wiggler to produce a substantially two-dimensional synchrotron beam that will produce the entire array of microbeams in a single exposure and will not require line-by-line production of the array. FIG. 9 is an end view of a patent being irradiated with multiple arrays of microbeams delivered by a gantry according to the present invention.

Figure 10:
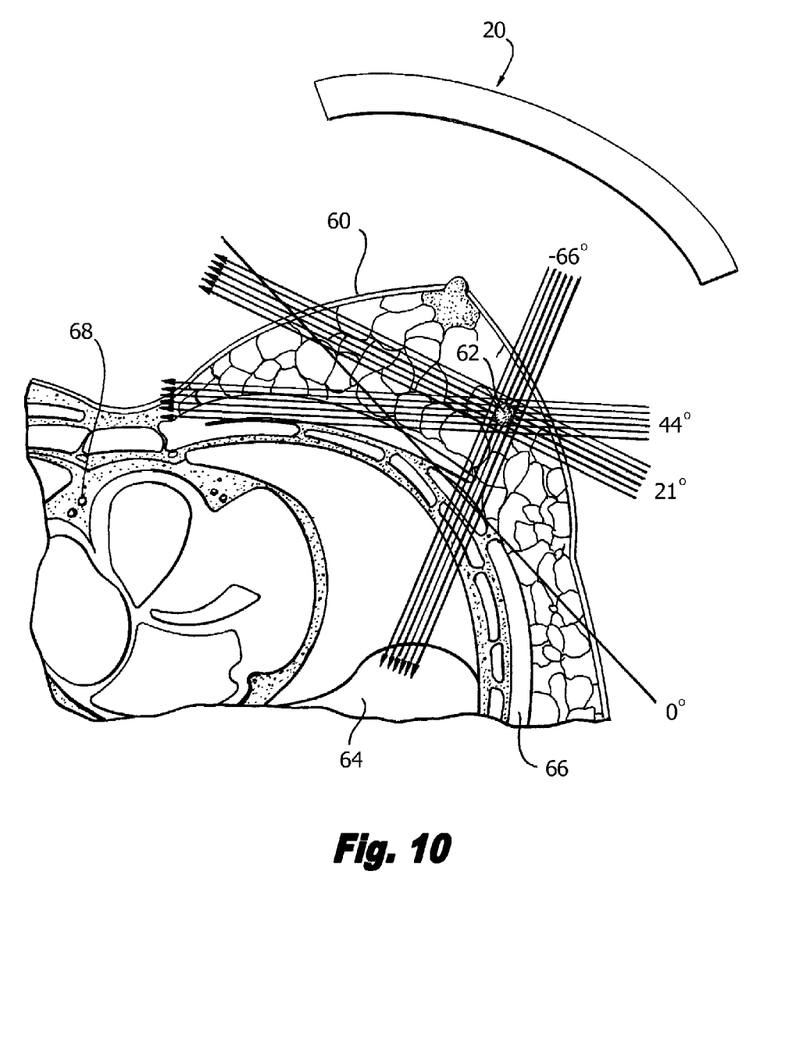
FIG. 10 is a cross-sectional view of the x-ray microbeam delivery device of the present invention being implemented to treat breast cancer.

Turning now to FIG. 10, the hemispherical geometry of the gantry 20 of the present invention is particularly well suited for the treatment of the primary breast cancer. In particular, the geometry of the breast 60 lends itself in a perfect way to the hemispherical geometry of the SMRT gantry 20 for irradiating a tumor 62 within the breast. Also, a major problem with conventional radiation therapy of the tumors of the breast 60, namely the dose to the lungs 64, could be avoided by reducing the beam's energy so that most of it will stop in the chest wall 66. This can be achieved due to the small tissue depth of most of the breast tumors. A median beam energy of about 90 keV, with a tissue-half-values layer of about 3 cm, will reduce the incident dose perpendicular to the chest by at least 4-fold past the chest wall. In particular, the given titled angles of the ten radiation ports 21, 22, 23, 24, 25 of SMRT gantry 20 of the present invention, with respect to the axis perpendicular axis (three with clustered around the tilt angle of 26° and seven around the title angle of 65°) is advantageous. This is because the attenuation in the chest wall of the incident angles with respect to the chest wall, i.e., the seven angles clustered around 65°, will be large, essentially eliminating the risk of the radiation damage to the lungs 64.

Moreover, because of the movement of the chest with the breathing cycle, the SMRT gantry 20 of the present invention preferably utilizes an image guided treatment method, and its patient's couch positioning is preferably gated with the respiratory cycle. Furthermore, because shorter irradiation times will lower the risk of inadvertent tissue movement, the synchrotron method may be more suitable than the x-ray tube technique for treating primary breast tumors.

The dose to the normal tissues will be distributed nearly evenly over half a sphere, thus further reducing the impact upon normal tissue. Half of the ports have a shallow incident angle such that the radiation misses the lungs 64 and heart 68. For those ports with steeper angles, the beam's energy can be reduced to lower the dose's depth penetration. It will be a single-dose-fraction therapy. The ten irradiations can be given either in one session, i.e., a single dose fraction, or at the most in five sessions, i.e., five dose fractions (i.e., the two interlacing arrays in each of the five orthogonal pairs of ports must be given in one session for targeting precision).

For an x-ray-tube-based SMRT systems, in all of the embodiments described above, one important consideration in designing the beam patterns, especially for the system's clinical applications, is that the beams are slightly diverging. This is because the source cannot be positioned very far from the microbeam collimator (and thus the subject) without the loss of beam's intensity. The divergence angle for each pencil microbeam differs from the others in the array, and is determined by the right-angle (transverse) distance of the microbeam from the center of the array. For example, for a 1-m source-to-collimator distance and 2-cm distance of the beam from the center of the arrays (i.e., the edge beam in treating a 4-cm target), the divergence angle is arctan (1/50), which is 1.14°, which leads to a 0.8-mm transverse displacement of the pencil beam. This displacement prevents exact "beam interlacing" with planar beams of 0.7 mm thickness and 1.4 mm beam spacing without having some overlaps between the adjacent beams.

Another important consideration for clinical implementation is that each treatment session (or dose-fractionation session) must be completed in about 30 minutes. This is also an important constraint because of the relatively low dose rate from each tube, which is only 1-5 Gy/minute at 1-m distance from the source depending on the amount of beam filtration. For applications with shallow targets, where lower beam energy is acceptable, the tube's high voltage can be reduced (and accordingly, the current on the tube will be increased), together with a possible decrease in the beam filtration, to increase the dose rate.

SMRT is a preferred treatment method for essentially all types of malignant and benign tumors, as well as for ablating the focal point of non-cancerous disorders such as the neurological targets, which are treated today by surgery or conventional radiation therapy. An example for the latter is the ablation of the epileptogenic foci.

The two SMRT methods based on x-ray tubes and synchrotron sources both have advantages and disadvantages with respect to each other. The x-ray-tube system has several advantages over synchrotron sources: a) all ten irradiations can be administered simultaneously; b) the patient's coach can stay stationary for the entire treatment; and c) the system can be installed in each large hospital. On the other hand, the synchrotron-based SMRT has the advantages of a) producing "sharper" beams with essentially no beam penumbra and/or beam divergence, and b) the dose rate will be very high, up to hundreds of Gy/s, thus shortening the treatment time for each port.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

The invention claimed is:

1. A radiation delivery gantry comprising:
a support frame; and
a plurality of microbeam delivery devices supported on said support frame in a hemispherical arrangement, each of said microbeam delivery devices being adapted to deliver at least one microbeam of radiation along a microbeam delivery axis, wherein said microbeam delivery axes of said plurality of microbeam delivery devices cross within a common target volume.

2. A radiation delivery gantry as defined in claim 1, wherein each of said microbeam delivery devices is an orthovoltage x-ray tube, and said radiation is x-ray radiation.

3. A radiation delivery gantry as defined in claim 1, wherein said plurality of microbeam delivery devices comprises at least one pair of orthogonally arranged devices, wherein said microbeam delivery axes of said pair cross within the target volume at a ninety degree angle.

4. A radiation delivery gantry as defined in claim 3, wherein said plurality of microbeam delivery devices comprises five pairs of orthogonally arranged devices.

5. A radiation delivery gantry as defined in claim 1, wherein said microbeam delivery axes of adjacent microbeam delivery devices cross within the target volume at about a forty-five degree angle.

6. A radiation delivery gantry as defined in claim 1, wherein each of said microbeam delivery devices is adapted to deliver a two-dimensional array of substantially parallel cylindrical microbeams to the target volume.

7. A radiation delivery gantry as defined in claim 6, wherein said cylindrical microbeams have a diameter less than 1 mm and are spaced less than 3 mm on center.

8. A radiation delivery gantry as defined in claim 3 wherein each of said microbeam delivery devices of said at least one orthogonally arranged pair is adapted to deliver a two-dimensional array of substantially parallel cylindrical microbeams to the target volume, said arrays of microbeams interlacing within the target volume.

9. A radiation delivery gantry as defined in claim 8, wherein said microbeam arrays comprise a first array including at least a first and a second cylindrical microbeam, said first and second microbeams defining two parallel, spatially distinct microbeam paths, and a second array including at least a third microbeam defining a third microbeam path, wherein said first and second microbeam arrays are interlaced substantially only within the target volume, whereby said third microbeam path is orthogonal and laterally translated with respect to said first and second microbeam paths, and whereby said third microbeam path crosses between but does not intersect with said first and second microbeam paths to form a substantially continuous broad beam of radiation substantially only within the target volume.

10. A radiation delivery gantry as defined in claim 6, wherein said microbeam delivery devices are hemispherically arranged to deliver said two-dimensional arrays in a pattern covering a continuous solid angle of $2\pi$ steradian around the target volume.

11. A method for delivering x-ray radiation comprising the step of aiming an array of substantially parallel, cylindrical x-ray microbeams at a target from a plurality of angularly spaced directions with respect to said target, said arrays defining a hemispherical arrangement of delivery ports around the target.

12. A method as defined in claim 11, wherein said x-ray microbeams are provided by a fixed synchrotron source and said aiming step comprises the step of tilting a patient bed different angles in front of said array for implementing different irradiation ports.

13. A method as defined in claim 11, wherein said x-ray microbeams are provided by a plurality of orthovoltage x-ray tubes.

14. A method as defined in claim 11, wherein said hemispherical arrangement comprises five pairs of orthogonally arranged ports.

15. A method as defined in claim 11, wherein each of said arrays comprises substantially parallel cylindrical microbeams arranged in a two-dimensional pattern of rows and columns.

16. A method as defined in claim 15, wherein said cylindrical microbeams have a diameter less than 1 mm and are spaced less than 3 mm on center.

17. A method as defined in claim 11 wherein said wherein said microbeam arrays from any two adjacent ports cross within the target volume at about a forty-five degree angle.

18. A method as defined in claim 15, wherein said microbeam ports are hemispherically arranged to deliver said two-dimensional arrays in a pattern covering a continuous solid angle of $2\pi$ steradian around the target volume.

19. A method for treating breast cancer comprising the steps of:
providing a plurality of x-ray microbeam delivery ports in a hemispherical arrangement around a breast having a tumor, each of said delivery ports being adapted to deliver at least one x-ray microbeam along a microbeam delivery axis, wherein said microbeam delivery axes of said plurality of delivery ports cross within the breast tumor; and
delivering at least one x-ray microbeam from each of at least one pair of orthogonally arranged delivery ports into the breast tumor, wherein said microbeam delivery axes of said pair cross within the breast tumor at a ninety degree angle.

20. A method as defined in claim 19, wherein said plurality of microbeam delivery ports comprises five pairs of orthogonally arranged x-ray tubes.

21. A method as defined in claim 19, wherein said microbeam delivery axes of adjacent microbeam delivery ports cross within the target volume at about a forty-five degree angle.

22. A method as defined in claim 19, wherein said microbeam delivery step comprises the step of simultaneously delivering at least two, two-dimensional arrays of substantially parallel cylindrical microbeams in the tumor, said arrays of microbeams interlacing within the tumor.

23. A method as defined in claim 22, wherein said cylindrical microbeams have a diameter less than 1 mm and are spaced less than 3 mm on center.

24. A method as defined in claim 22, wherein said microbeam arrays comprise a first array including at least a first and a second cylindrical microbeam, said first and second microbeams defining two parallel, spatially distinct microbeam paths, and a second array including at least a third microbeam defining a third microbeam path, wherein said first and second microbeam arrays are interlaced substantially only within the tumor, whereby said third microbeam path is orthogonal and laterally translated with respect to said first and second microbeam paths, and whereby said third microbeam path crosses between but does not intersect with said first and second microbeam paths to form a substantially continuous broad beam of radiation substantially only within the tumor.

25. A method as defined in claim 22, wherein said microbeam delivery ports are hemishperically arranged to deliver said two-dimensional arrays in a pattern covering a continuous solid angle of $2\pi$ steradian around the tumor.

* * * * *